United States Patent [19]

Kiel et al.

[11] Patent Number: 5,089,385
[45] Date of Patent: Feb. 18, 1992

[54] METHOD OF CULTURING CELLS IN A FLOW-THROUGH CELL CULTIVATION SYSTEM

[75] Inventors: Johnathan L. Kiel; David N. Erwin, both of San Antonio; David M. Simmons, Brooks AFB, all of Tex.

[73] Assignee: The United States of America as represented by the Secretary of the Air Force, Washington, D.C.

[21] Appl. No.: 521,064

[22] Filed: May 7, 1990

Related U.S. Application Data

[62] Division of Ser. No. 56,034, Jun. 1, 1987, Pat. No. 5,028,541.

[51] Int. Cl.$^5$ ............................................. C12Q 3/00
[52] U.S. Cl. .................................. 435/3; 435/173; 435/240.1; 435/240.24; 435/240.25; 435/813
[58] Field of Search ............... 435/3, 173, 174, 240.1, 435/240.2, 240.24, 240.25, 243, 284, 286, 288, 290, 813

[56] References Cited

U.S. PATENT DOCUMENTS

| | | | |
|---|---|---|---|
| 1,140,818 | 5/1915 | Henri et al. | |
| 2,196,361 | 4/1940 | Liebesny et al. | 195/79 |
| 3,590,634 | 7/1971 | Pasternak et al. | 73/159 |
| 4,225,671 | 9/1980 | Puchinger et al. | 435/71 |
| 4,327,180 | 4/1982 | Chen | 435/173 |
| 4,435,508 | 3/1984 | Gabridge | 435/284 |
| 4,464,330 | 8/1984 | Speir et al. | 376/109 |
| 4,508,819 | 4/1985 | Rose | 435/1 |
| 4,649,117 | 3/1987 | Familletti | 435/313 |

FOREIGN PATENT DOCUMENTS

| | | | |
|---|---|---|---|
| 1598245 | 8/1970 | France | 435/284 |
| 8600636 | 1/1986 | PCT Int'l Appl. | |
| 8702705 | 5/1987 | PCT Int'l Appl. | |

*Primary Examiner*—David L. Lacey
*Assistant Examiner*—William H. Beisner
*Attorney, Agent, or Firm*—Fredric L. Sinder; Donald J. Singer

[57] ABSTRACT

A flow-through cell cultivation apparatus and method is described. The flow-through cell cultivation system comprises a flowcell, a chamber inside the flowcell for holding cells, and a flowcell holder. The flowcell has a lower intake port for flowing liquid nutrient through a cellbed inside the flowcell and an upper outlet port for flowing the liquid nutrient out of the flowcell. The flowcell also includes a chuck for receipt of a thermal probe. The probe is made of electromagnetically non-interactive material. The flowcell is enclosed inside the flowcell holder. The flowcell holder includes a pair of intake ports into a cavity having an open end at the flowcell for turbulently flowing a temperature controlled gas against the flowcell. The cavity has rough walls to promote the turbulent flow. The flowcell holder includes an exhaust port for flowing the gas out of the flowcell holder which also serves as a port for another thermal probe. A one-way valve prevents flow of the liquid nutrient out of the chamber through the intake port. Temperature controlled air is supplied to the flowcell holder by dividing air from an air supply into two conduits. One conduit travels through a coil inside a refrigerated liquid bath and the other through a coil inside a heated liquid bath. The heated and cooled air are recombined to make an even temperature air supply which is then divided once more to provide the two air supplies for creating a turbulent supply of temperature controlled air through the two flowcell holder intake ports. The flowcell may include on one side a semi-permeable membrane for introducing a gas/liquid interface to the cellbed.

3 Claims, 3 Drawing Sheets

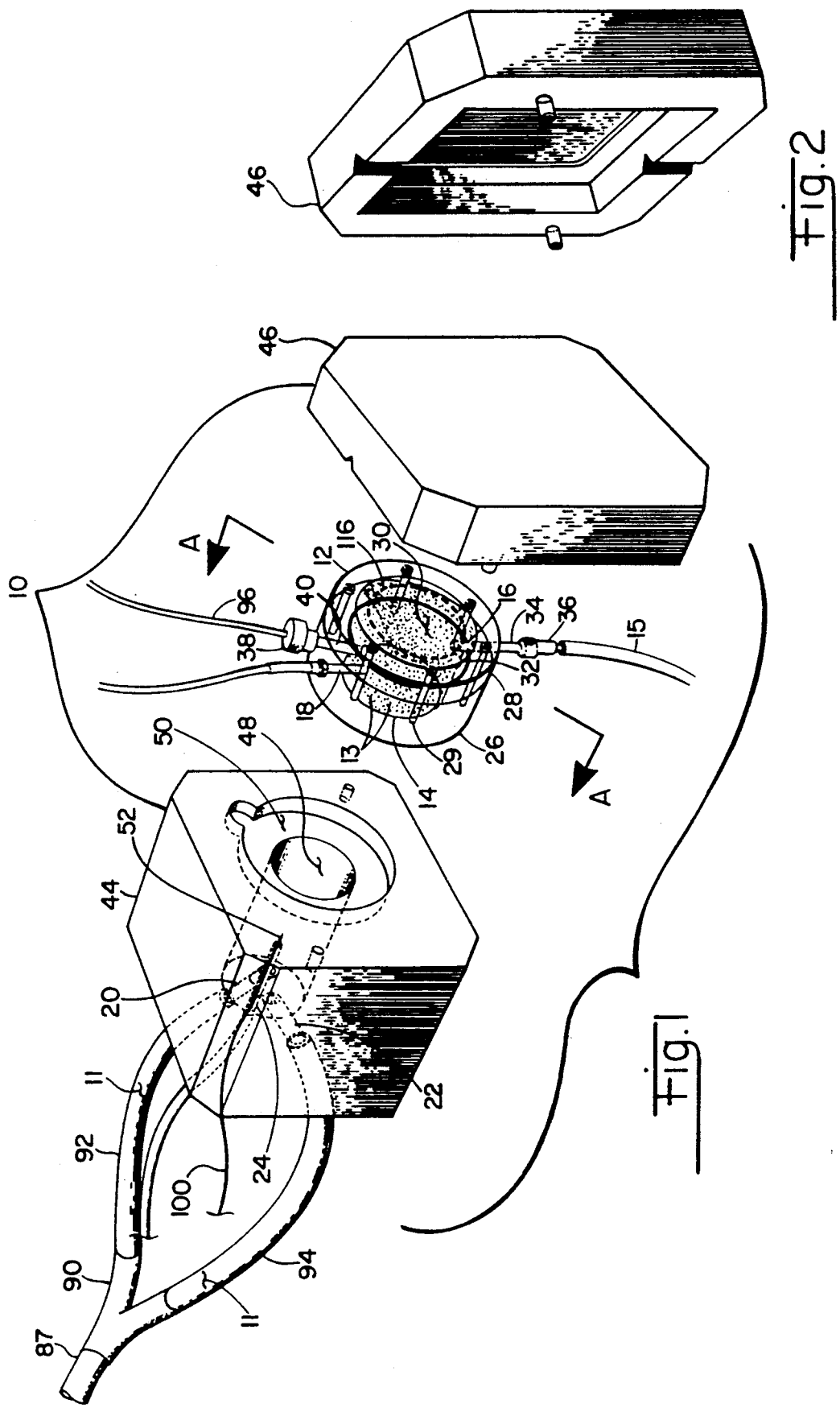

METHOD OF CULTURING CELLS IN A FLOW-THROUGH CELL CULTIVATION SYSTEM

RIGHTS OF THE GOVERNMENT

The invention described herein may be manufactured and used by or for the Government of the United States for all governmental purposes without the payment of any royalty.

This is a division of application Ser. No. 07/056,034, filed June 1, 1987, now U.S. Pat. No. 5,028,591.

BACKGROUND OF THE INVENTION

The present invention relates generally to cell incubators, and more specifically to a novel flow-through chamber for exposing cells immobilized on microcarrier beads to precisely controlled temperatures and to radiation.

In vitro (outside a living organism) culturing of cells in cell incubators provides material needed for research in pharmocology, physiology, toxicology and radiation effects. Cell incubators also provide an environment for testing the response of living cells to exposure of drugs, especially new anti-cancer drugs, to exposure of toxicological materials and to exposure of radiation, without requiring experiments on more sentient living things. Cell incubators may also be used to produce valuable cellular products such as monoclonal antibodies and recombinant DNA products.

Cell incubators must have precise and rapid response temperature control. Current cell incubators using water jackets for temperature control can respond only sluggishly to temperature changes and are generally unsuitable for careful control of cell culture temperature.

Cell incubators must also provide a suitable carrier for supporting living cells. Present cell incubators using fibers as cell carriers do not have sufficient surface area to culture large amounts of cells. Further, they are restricted by the limited commercial availability of different fibers and fiber coatings suitable for culturing a large variety of different cell types.

The usefulness of cell incubators is greatly enhanced if they can be adapted to expose cells to various gas mixtures. Cell incubators have this feature require precise control of gas mixtures at the liquid/gas interface between the gas and a nutrient medium.

It is seen, therefore, that there is a need for an improved cell cultivation system for in vitro culturing of cells without the limitations of prior art cell incubators.

It is, therefore, a principal object of the present invention to provide a flow-through cell cultivation system that provides precise and rapid-response temperature control and that is suitable for a wide variety of cell incubator uses.

Another object of the present invention is to provide a cell cultivation system particularly applicable to non-ionizing and ionizing radiation studies.

A further object of the present invention is to provide a cell cultivation system adaptable to a variety of other uses, including gas exposure and production of cellular products.

A feature of the present invention is that it uses micro-carrier beads available in a large variety of commercially available sizes and types, thereby increasing the number of cell strains and lines available for potential applications.

An advantage of the present invention is that it provides a low-pressure fluidized bed which prevents plugging and backflow of the beads.

A further advantage of the present invention is that it treats cells very delicately thereby preventing cell damage and promoting cell growth.

SUMMARY OF THE INVENTION

The present invention provides continuous cell culturing under highly controlled physical and chemical conditions and the continuous production of biochemical products under these conditions.

The unique discovery of the present invention is that cell culture heating by microwave radiation balanced by a supply of temperature controlled air provides a particularly precise and responsive temperature control means suitable for both radiation studies and production of biological products. The use of electromagnetically non-interactive materials makes possible radiofrequency radiation (RFR) studies.

Another discovery of the present invention is that supplying a nutrient medium through a bottom mounted intake port provides a non-agitating perfusion of nutrient through incubating cellular material.

Accordingly, the present invention is directed to a flow-through cell cultivation system comprising a flowcell, a chamber for holding cells inside the flowcell, and a flowcell holder. The flowcell has a lower intake port for flowing liquid nutrient through a cellbed inside the flowcell and an upper outlet port for flowing the liquid nutrient out of the flowcell. The flowcell is enclosed inside the flowcell holder which includes intake port means for flowing a temperature controlled gas into a cavity inside the flowcell holder and an exhaust port for flowing the gas out of the flowcell holder cavity. The cavity has an end open to the flowcell. The system further includes means for creating a turbulent flow of the gas within the cavity.

The turbulent flow creating means may comprise a rough cavity wall surface. The turbulent flow may also be effected by intake port means comprising a plurality of intake ports offset to create the turbulent flow.

The invention may additionally include means for creating an electromagnetic field around the flowcell and flowcell holder. The means for creating an electromagnetic field may comprise a circularly polarized waveguide.

The invention may further include a port through the flowcell for receipt of a thermal probe. The flowcell holder may also have a port for receiving a thermal probe and the port may be coaxial with the flowcell holder exhaust port.

A one-way valve may be added to the flowcell intake port for preventing flow of the liquid nutrient out of the chamber through the intake port.

The invention may further include a semi-permeable membrane between the inside of the flowcell chamber and the cavity open end.

The invention further includes a source of temperature controlled air comprising a gas supply connected to a first Y-fitting connected through a first conduit; a first gas valve connected to the first Y-fitting through a second conduit; a second gas valve connected to the first Y-fitting through a third conduit; a fourth conduit connected to the first gas valve whereby the first air valve controls the flow of gas from the second conduit to the fourth conduit; a fifth conduit connected to the second gas valve whereby the second gas valve controls the flow of gas from the third conduit to the fifth conduit; a cooled liquid bath enclosing part of the fourth conduit for cooling the gas flowing through the fourth conduit; a heated liquid bath enclosing part of the fifth conduit for heating the gas flowing through the fifth conduit; a second Y-fitting connecting the fourth and fifth conduit to a sixth conduit so that the cooled gas from the fourth conduit is mixed with the heated gas from the fifth conduit in the sixth conduit; and, a third Y-fitting connecting the sixth conduit to a seventh and eighth conduit, wherein the seventh and eighth conduits are respectively connected to at least two flowcell holder intake ports.

The invention additionally includes the method of cultivating cells by use of the described apparatus.

DESCRIPTION OF THE DRAWINGS

The present invention will be more clearly understood from a reading of the following detailed description in conjunction with the accompanying drawings wherein:

FIG. 1 is an exploded perspective view of a flowcell holder and flowcell for a flow-through cell cultivation system according to the teachings of the present invention;

FIG. 2 is a perspective view of the inside of the flowcell holder cover shown in FIG. 1;

DETAILED DESCRIPTION

Figure 3:
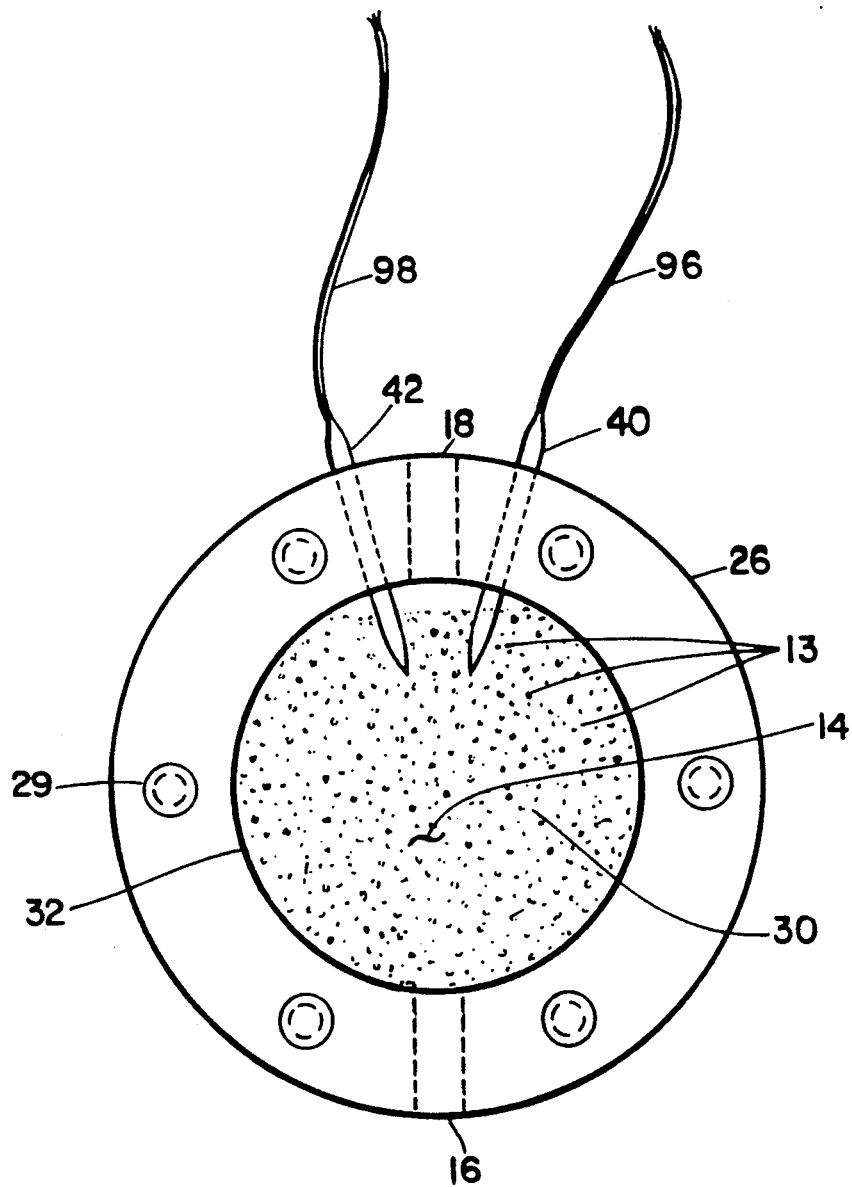
FIG. 3 is a view of the flowcell along line A—A of FIG. 1 showing the optional use of a second thermal probe; and, FIG. 4 is a schematic view of a circularly polarized waveguide and a thermal control system according to the teachings of the present invention.

Referring now to FIG. 1 to the drawings, there is shown an exploded perspective view of a flowcell holder 10 and flowcell 12 for a flow-through cell cultivation system. A porous bed 14 of micro-carrier beads 13 is enclosed by flowcell 12 which is in turn enclosed inside flowcell holder 10. Cells to be cultured are immobilized on the surfaces of the beads. A liquid nutrient medium 15 enters intake port 16, flows diffusely through cell bed 14 and exits through outlet port 18. Cells 13 in cell bed 14 are more densely packed than as shown in FIGS. 1 and 3, which have been drawn to avoid obscuring other drawing details. Temperature controlled air 11 enters flowcell holder 10 at intake ports 20 and 22 and exits at exhaust port 24 to turbulently flow the temperature controlled air over flowcell 12.

Flowcell 12 comprises primarily a flowcell housing 26 and a cover 28 together defining a chamber 30. An O-ring 32 provides a positive seal between cover 28 and housing 26. An intake fitting 34 to intake port 16 includes a one-way check valve 36 to prevent backflow of the nutrient medium. A chuck 38 secures a thermal probe 40 for monitoring the temperature inside chamber 30. Flowcell 12 may include an additional thermal probe 42 as shown in the FIG. 3 view of flowcell 12. Flowcell 12 is made of a clear acrylic plastic, including screws 29 used to attach cover 28 to housing 26. Other suitable materials may be chosen, the primary requirement being that they are electromagnetically non-interactive.

Flowcell holder 10 comprises primarily a housing 44 and a cover 46 together enclosing air cavity 48 and flowcell holding compartment 50. Holding compartment 50 is complementarily shaped to hold flowcell 12 firmly in position when cover 46 is attached to housing 44. Intake ports 20 and 22 are offset to create a turbulent flow inside cavity 48. The inside walls of cavity 48 are made rough (not shown) to prevent laminar flow and to promote the formation of turbulent flow. The turbulent flow is an important factor in the successful use of the invention. Flowcell holder 10 also includes a thermal probe 52 coaxial with exhaust port 24. Flowcell holder 10 is made of a foamed polystyrene, but may be made of other both electromagnetically non-interactive and insulating materials. If the heat loss through the walls of flowcell holder 10 is too great, the temperature inside the flowcell becomes more difficult to control.

Figure 4:
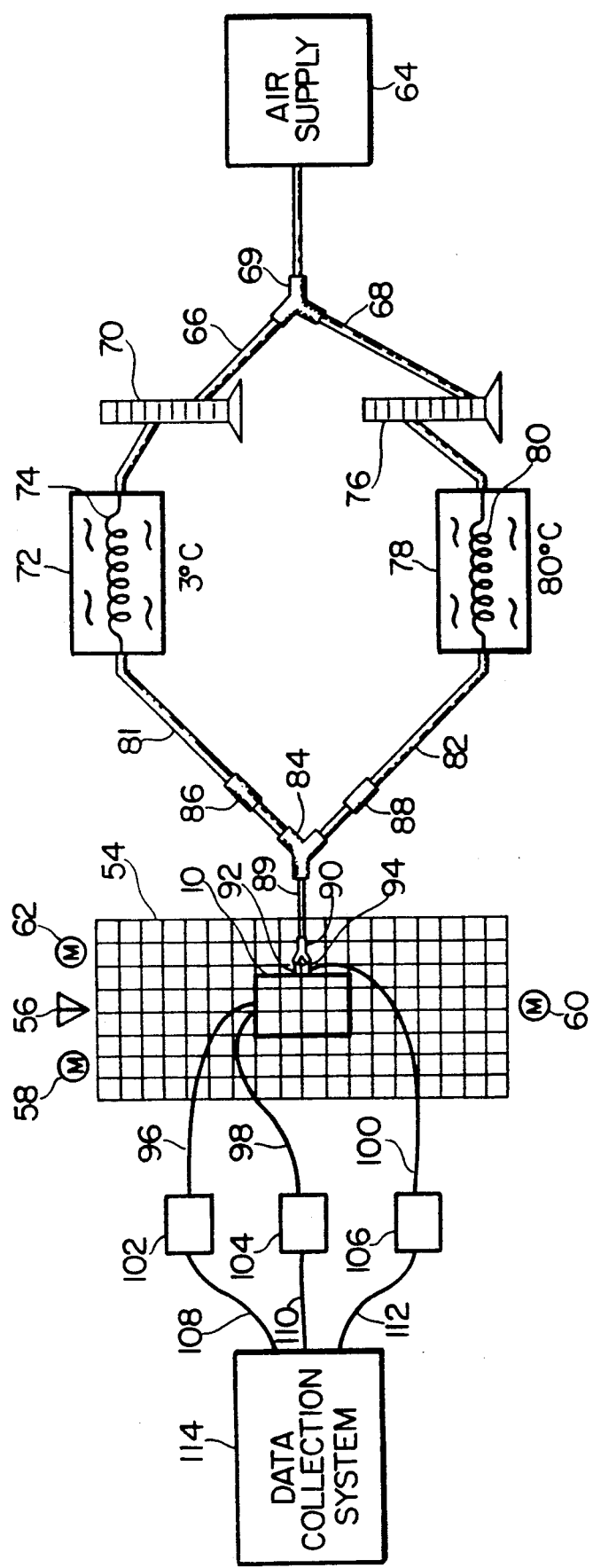

Flowcell holder 10 and flowcell 12 are positioned inside a circularly polarized wire cage waveguide 54 shown schematically in FIG. 4. Radiofrequency (RF) radiation is introduced by a RF power source 56. The amount of RF radiation power present within waveguide 54 is measured by RF power meter 58 measuring the RF power originally entering waveguide 54, RF power meter 60 measuring the RF power leaving the opposite end of waveguide 54 and RF power meter 62 measuring the RF power reflected back out of waveguide 54. In addition to these measurements of RF power from waveguide 54, the heating and cooling curves from the output of the thermal probes provide a more accurate calorimetric measurement of the heat absorbed within the flowcell.

Air to be cooled or heated and then delivered to cavity 48 of flowcell holder 10 is supplied from air supply 64. The air is separated into conduits 66 and 68 by a Y-fitting 69. Conduit 66 directs air to an air flow valve and meter 70 which controls the delivery of air to a liquid bath 72 kept refrigerated to 3° C. A coiled copper tube 74 increases the transfer rate of heat out of the air into liquid bath 72 to cool the incoming air. Conduit 68 directs air to an air flow valve and meter 76 which controls the delivery of air to a liquid bath 78 kept heated to 80° C. A coiled stainless steel tube 80 increases the transfer rate of heat out of the liquid bath 78 to heat the incoming air. Coiled tubes 74 and 80 may be made of any suitable material having a high rate of heat transfer. Cooled air from bath 72 and heated air from bath 78 are directed through respective conduits 81 and 82 to mix at Y-fitting 84 to create an even temperature output of temperature controlled air 11 through conduit 89. Check valves 86 and 88 are an additional control on the delivery of air. Another Y-fitting 90 separates the mixed air from Y-fitting 84 into conduits 92 and 94 to separately enter intake ports 20 and 22 to create the previously described turbulent flow against flowcell 12.

Leads 96, 98 and 100 from respective thermal probes 40, 42 and 52 are connected to respective thermal probe controllers 102, 104 and 106. Leads 108, 110 and 112 extend to a data collection system 114 for monitoring of air and cell bed 14 temperatures. Thermal probes 40, 42 and 52 are high resistance carbon probes that do not interact with the microwave or RF radiation inside waveguide 54. Leads 96, 98 and 100 are also electromagnetically non-interactive. Vitek brand thermal probes, now available from BSD Medical Corporation, Salt Lake City, Utah, have worked successfully. Thermal probe 40 may be extended or retracted through chuck 38 to sample temperatures at different positions in cell bed 14. Probe 42 may be used to provide a reference measurement.

A description of the use of the invention in performing studies on the effects of microwave radiation on various living cells will explain its operation. Selected cells are immobilized on the surfaces of micro-carrier beads 13 by any of various methods known to those with skill in the art to form a slurry. The slurry is placed inside housing 26 of flowcell 12 and cover 28 secured to hold the slurry in place as cell bed 14. Cell bed 14 nearly fills flowcell 12, leaving a small airspace at its top beneath outlet port 18. Nutrient medium 15 is flowed through cell bed 14 by a peristalic pump (not shown) at rates from 0.1 to 0.6 ml/min. In a test cell 12 having a chamber 30 volume of 23.6 ml (diameter=5 cm, depth=1.2 cm), the optimum bed perfusion rate was found to be 0.3 ml/min. The flow rate is set so that individual beads are just separated by the flow and channels are not formed. Tests with dyes injected into medium 15 have shown a fanning out of the dye (delta effect) indicating good diffusion. Very little turbulence has been observed. The medium is intended to flow around the cells and not the cells through the medium. Escape of beads 13 through outlet port 18 is prevented primarily by gravity. Escape of beads 13 through intake port 16 is prevented by the force of medium 15 flow and ultimately by one-way check valve 36.

Flowcell 12 is placed inside holding compartment 50 of flowcell holder 10 and cover 46 secured to housing 44. The entire flowcell holder 10 and flowcell 12 assembly is positioned inside waveguide 54 which produces circularly polarized 2450 MHz microwave radiation. The most direct effect of the microwave radiation on the cells is microwave heating. Without means for maintaining a constant temperature inside cell bed 14, the effects from heating would mask more subtle radiation effects and possibly destroy the cells. Mixing cooled and heated air by modulating air flow valves 70 and 76 provides temperature controlled air to turbulently flow over and around flowcell 12. The required respective settings of valves 70 and 76 are determined by monitoring the temperatures of the air and cell bed 14 with thermal probe controllers 102, 104 and 106. Data collection system 114 provides, if desired, a continuous record of the temperatures measured by the probes.

In operation, the disclosed cell incubator has successfully maintained very precise temperatures inside cell bed 14 and adjustment of flow values 70 and 76 have produced very rapid changes of cell bed 14 temperatures. It was found in one experiment, for example, that the cell chamber temperature could be changed from 25° C. to 37° C. in 30 seconds and that the temperature could be held constant at temperatures ranging from 25° C. to 45° C. in the presence of specific absorption rates of microwave radiation up to 100 W/kg.

The ability of the disclosed cell incubator to control cell bed temperature in the presence of microwave heating makes it particularly adaptable for other uses. By using microwave heating and air temperature control together, more precise and responsive temperature control inside cell bed 14 can be maintained than by either means alone and is a great improvement over the prior art. Experiments have shown that adverse cellular effects from the microwave radiation is either non-existent or has not to date shown any contaminating effect on growing or tested cells.

Flowcell 12 may be positioned inside flowcell holder 10 with its cover facing either toward or away from air cavity 48. Flowcell cover 28 may be replaced by a cover holding a semipermeable membrane, indicated by dashed line 116, and turned over with flowcell housing 26 to make a liquid/gas interface between the air inside cavity 48 and liquid nutrient medium 15 flowing through cell bed 14. A supply of a pre-selected gas or gases would replace air supply 64. Very precise control of the gas mixture at the liquid/gas interface may be obtained.

Those with skill in the art will see that the disclosed flow-through cell cultivation system may be used in a variety of different ways to achieve useful results. For example, toxic material may be introduced into the nutrient medium by injection through a sidearm and septum into tubing leading to intake port 16. Also, small micro-colonies of cells, immobilized enzymes, large cells and proteins may be cultured inside the flowcell without beads. Scaling up of the disclosed flowcell would make it suitable for producing large amounts of cellular products such as monoclonal antibodies and recombinant DNA products. The disclosed cell cultivation system will find valuable use in any application where cell incubation is part of the application process.

The disclosed cell cultivation system successfully demonstrates the use of a balanced supply of temperature controlled air and microwave heating to control the temperature of the cell culture. It additionally successfully demonstrates the use of a combination of a bottom mounted intake port, a slurry of cell culture material and gravity to achieve a successful perfusion of nutrient medium through the cell bed without damaging cells. Though the disclosed use is specialized, it will find application in other areas of process control of temperature and infusion.

Those with skill in the art will readily see modifications to the disclosed cell cultivation system to improve its operation. For example, flowcell holder cover 46 may be modified to permit temperature controlled air to circulate completely around flowcell 12 while still helping to hold flowcell 12 in place. Other equivalent means for separating gas flows may replace the disclosed Y-fittings. It is understood that certain other modifications to the invention as described may be made, as might occur to one with skill in the field of the invention, also within the intended scope of the claims. Therefore, all embodiments contemplated have not been shown in complete detail. Other embodiments may be developed without departing from the spirit of the invention or from the scope of the claims.

We claim:

1. A method for cultivating cells, comprising the steps of:
   (a) providing a flowcell enclosing a chamber holding cells inside the flowcell, wherein the chamber has the shape of a cylindrical section about a horizontal axis;
   (b) providing a flowcell holder enclosing the flowcell;
   (c) flowing a liquid nutrient medium into the bottom of the flowcell chamber and out the top of the flowcell chamber;
   (d) flowing a temperature controlled gas through the flowcell holder to turbulently flow against the flowcell;
   (e) providing an electromagnetic field around the flowcell holder and flowcell for heating the cells; and,
   (f) controlling the electromagnetic field and the temperature and flow of the gas to balance the cell heating from the electromagnetic field against the temperature and flow of the gas to maintain a preselected temperature of the cells.

2. A method for cultivating cells, comprising the steps of:

(a) providing a flowcell enclosing a chamber holding a bed of micro-carrier beads carrying attached cells;

(b) providing a flowcell holder enclosing the flowcell;

(c) flowing a liquid nutrient medium into the bottom of the flowcell chamber and out the top of the flowcell chamber at a selected flow rate, wherein the flow rate is selected so that the micro-carrier beads are just separated and channels are not formed;

(d) flowing a temperature controlled gas through the flowcell holder to turbulently flow against the flowcell;

(e) providing an electromagnetic field around the flowcell holder and flowcell for heating the cells; and, (f) controlling the electromagnetic field and the temperature and flow of the gas to balance the cell heating from the electromagnetic field against the temperature and flow of the gas to maintain a preselected temperature of the cells.

3. The method for cultivating cells according to claim 2, wherein the chamber has the shape of a cylindrical section about a horizontal axis.

* * * * *